United States Patent
Yu et al.

(10) Patent No.: US 11,350,998 B2
(45) Date of Patent: Jun. 7, 2022

(54) MEDICAL INSTRUMENT HAVING TRANSLATABLE SPOOL

(71) Applicant: Auris Health, Inc., Redwood City, CA (US)

(72) Inventors: Alan Yu, Union City, CA (US); Jason Lee, Milpitas, CA (US)

(73) Assignee: Auris Health, Inc., Redwood City, CA (US)

( * ) Notice: Subject to any disclaimer, the term of this patent is extended or adjusted under 35 U.S.C. 154(b) by 470 days.

(21) Appl. No.: 16/555,723

(22) Filed: Aug. 29, 2019

(65) Prior Publication Data
US 2019/0380797 A1 Dec. 19, 2019

Related U.S. Application Data

(63) Continuation of application No. 15/388,955, filed on Dec. 22, 2016, now Pat. No. 10,398,518, which is a (Continued)

(51) Int. Cl.
*A61B 34/30* (2016.01)
*A61B 34/00* (2016.01)
(Continued)

(52) U.S. Cl.
CPC ............ *A61B 34/30* (2016.02); *A61B 1/0052* (2013.01); *A61B 1/0057* (2013.01);
(Continued)

(58) Field of Classification Search
CPC ... A61B 34/30; A61B 1/00147; A61B 1/0052; A61B 1/0057; A61B 34/71; A61B 46/10;
(Continued)

(56) References Cited

U.S. PATENT DOCUMENTS

| 2,556,601 A | 6/1951 | Schofield |
| 2,566,183 A | 8/1951 | Forss |

(Continued)

FOREIGN PATENT DOCUMENTS

| CN | 1846181 | 10/2006 |
| CN | 1857877 | 11/2006 |

(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

*Primary Examiner* — Amber R Stiles
(74) *Attorney, Agent, or Firm* — Chang & Hale LLP

(57) ABSTRACT

Medical instruments having a translatable spool are disclosed. In one aspect, a medical instrument configured for use with a robotic system includes an instrument base configured to couple to a robotic drive mechanism of the robotic system and an elongate shaft coupled to the instrument base. The elongate shaft has a distal end. The medical instrument also includes a pull wire fixedly coupled to the distal end of the elongate shaft, the pull wire being configured to actuate the elongate shaft, and a rotatable spool in the instrument base. The rotatable spool is configured to direct the pull wire to the elongate shaft at an angle. The rotatable spool is configured to translate in coordination with actuation of the elongate shaft to control the angle of the pull wire relative to the elongate shaft.

20 Claims, 14 Drawing Sheets

Related U.S. Application Data continuation of application No. 15/072,072, filed on Mar. 16, 2016, now Pat. No. 9,561,083.

(60) Provisional application No. 62/134,366, filed on Mar. 17, 2015.

(51) Int. Cl.
  *A61B 1/00* (2006.01)
  *A61B 1/005* (2006.01)
  *A61B 17/00* (2006.01)
  *A61B 46/10* (2016.01)

(52) U.S. Cl.
  CPC .......... *A61B 1/00147* (2013.01); *A61B 34/71* (2016.02); *A61B 46/10* (2016.02); *A61B 2017/0034* (2013.01); *A61B 2017/00323* (2013.01); *A61B 2034/301* (2016.02); *A61B 2034/303* (2016.02)

(58) Field of Classification Search
  CPC .. A61B 2017/00323; A61B 2017/0034; A61B 2034/301; A61B 2034/303
  See application file for complete search history.

(56) References Cited

U.S. PATENT DOCUMENTS

| | | | |
|---|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,572,325 A | 3/1971 | Bazell et al. |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,892,228 A | 7/1975 | Mitsui |
| 3,913,565 A | 10/1975 | Kawahara |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,294,234 A | 10/1981 | Matsuo |
| 4,351,493 A | 9/1982 | Sonnek |
| 4,357,843 A | 11/1982 | Peck et al. |
| 4,384,493 A | 5/1983 | Grunbaum |
| 4,392,485 A | 7/1983 | Hiltebrandt |
| 4,507,026 A | 3/1985 | Lund |
| 4,530,471 A | 7/1985 | Inoue |
| 4,555,960 A | 12/1985 | King |
| 4,607,619 A | 8/1986 | Seike et al. |
| 4,688,555 A | 8/1987 | Wardle |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro |
| 4,784,150 A | 11/1988 | Voorhies et al. |
| 4,846,791 A | 7/1989 | Hattler et al. |
| 4,857,058 A | 8/1989 | Payton |
| 4,869,238 A | 9/1989 | Opie et al. |
| 4,906,496 A | 3/1990 | Hosono et al. |
| 4,907,168 A | 3/1990 | Boggs |
| 4,945,790 A | 8/1990 | Golden |
| 4,967,732 A | 11/1990 | Inoue |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,207,128 A | 5/1993 | Albright |
| 5,217,002 A | 6/1993 | Katsurada |
| 5,234,428 A | 8/1993 | Kaufman |
| 5,251,611 A | 10/1993 | Zehel et al. |
| 5,256,150 A | 10/1993 | Quiachon et al. |
| 5,257,617 A | 11/1993 | Takahashi |
| 5,261,391 A | 11/1993 | Inoue |
| 5,277,085 A | 1/1994 | Tanimura et al. |
| 5,287,861 A | 2/1994 | Wilk |
| 5,313,934 A | 5/1994 | Wiita et al. |
| 5,350,101 A | 9/1994 | Godlewski |
| 5,386,818 A | 2/1995 | Schneebaum |
| 5,426,687 A | 6/1995 | Goodall et al. |
| 5,448,988 A | 9/1995 | Watanabe |
| 5,478,330 A | 12/1995 | Imran et al. |
| 5,482,029 A | 1/1996 | Sekiguchi |
| 5,489,270 A | 2/1996 | van Erp |
| 5,507,725 A | 4/1996 | Savage et al. |
| 5,524,180 A | 6/1996 | Wang et al. |
| 5,533,985 A | 7/1996 | Wang |
| 5,559,294 A | 9/1996 | Hoium et al. |
| 5,580,200 A | 12/1996 | Fullerton |
| 5,681,296 A | 10/1997 | Ishida |
| 5,704,534 A | 1/1998 | Huitema et al. |
| 5,709,661 A | 1/1998 | Van Egmond |
| 5,720,775 A | 2/1998 | Lamard |
| 5,741,429 A | 4/1998 | Donadio, III |
| 5,749,889 A | 5/1998 | Bacich et al. |
| 5,767,840 A | 6/1998 | Selker |
| 5,779,623 A | 7/1998 | Bonnell |
| 5,792,135 A | 8/1998 | Madhani et al. |
| 5,797,900 A | 8/1998 | Madhani |
| 5,842,390 A | 12/1998 | Bouligny |
| 5,855,583 A | 1/1999 | Wang et al. |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,910,129 A | 6/1999 | Koblish et al. |
| 5,921,968 A | 7/1999 | Lampropoulos et al. |
| 5,938,586 A | 8/1999 | Wilk |
| 5,938,587 A | 8/1999 | Taylor et al. |
| 5,967,934 A | 10/1999 | Ishida et al. |
| 6,012,494 A | 1/2000 | Balazs |
| 6,077,219 A | 6/2000 | Viebach |
| 6,084,371 A | 7/2000 | Kress et al. |
| 6,143,013 A | 11/2000 | Samson et al. |
| 6,154,000 A | 11/2000 | Rastegar et al. |
| 6,157,853 A | 12/2000 | Blume et al. |
| 6,171,234 B1 | 1/2001 | White et al. |
| 6,174,280 B1 | 1/2001 | Oneda |
| 6,185,478 B1 | 2/2001 | Koakutsu et al. |
| 6,197,015 B1 | 3/2001 | Wilson |
| 6,198,974 B1 | 3/2001 | Webster, Jr. |
| 6,234,958 B1 | 5/2001 | Snoke et al. |
| 6,272,371 B1 | 8/2001 | Shlomo |
| 6,289,579 B1 | 9/2001 | Viza et al. |
| 6,315,715 B1 | 11/2001 | Taylor et al. |
| 6,394,998 B1 | 5/2002 | Wallace et al. |
| 6,401,572 B1 | 6/2002 | Provost |
| 6,404,497 B1 | 6/2002 | Backman |
| 6,436,107 B1 | 8/2002 | Wang et al. |
| 6,464,632 B1 | 10/2002 | Taylor |
| 6,485,411 B1 | 11/2002 | Konstorum |
| 6,487,940 B2 | 12/2002 | Hart et al. |
| 6,491,626 B1 | 12/2002 | Stone et al. |
| 6,491,701 B2 | 12/2002 | Tierney et al. |
| 6,537,205 B1 | 3/2003 | Smith |
| 6,554,793 B1 | 4/2003 | Pauker et al. |
| 6,695,818 B2 | 2/2004 | Wollschlager |
| 6,716,178 B1 | 4/2004 | Kilpatrick et al. |
| 6,726,675 B1 | 4/2004 | Beyar |
| 6,746,422 B1 | 6/2004 | Noriega |
| 6,749,560 B1 | 6/2004 | Konstorum |
| 6,786,896 B1 | 9/2004 | Madhani et al. |

(56) References Cited

U.S. PATENT DOCUMENTS

| | | |
|---|---|---|
| 6,790,173 B2 | 9/2004 | Saadat |
| 6,827,710 B1 | 12/2004 | Mooney et al. |
| 6,827,712 B2 | 12/2004 | Tovey et al. |
| 6,837,846 B2 | 1/2005 | Jaffe |
| 6,908,428 B2 | 6/2005 | Aizenfeld |
| 6,921,362 B2 | 7/2005 | Ouchi |
| 6,958,035 B2 | 10/2005 | Friedman et al. |
| 7,008,401 B2 | 3/2006 | Thompson et al. |
| 7,044,936 B2 | 5/2006 | Harding |
| 7,130,700 B2 | 10/2006 | Gardeski et al. |
| 7,172,580 B2 | 2/2007 | Hruska et al. |
| 7,276,044 B2 | 10/2007 | Ferry et al. |
| 7,594,903 B2 | 9/2009 | Webler et al. |
| 7,615,042 B2 | 11/2009 | Beyar et al. |
| 7,635,342 B2 | 12/2009 | Ferry et al. |
| 7,645,230 B2 | 1/2010 | Mikkaichi |
| 7,645,231 B2 | 1/2010 | Akiba |
| 7,766,856 B2 | 8/2010 | Ferry et al. |
| 7,771,416 B2 | 8/2010 | Spiver et al. |
| 7,789,827 B2 | 9/2010 | Landry |
| 7,789,874 B2 | 9/2010 | Yu et al. |
| 7,930,065 B2 | 4/2011 | Larkin et al. |
| 7,938,809 B2 | 5/2011 | Lampropoulos et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,046,049 B2 | 10/2011 | Govari et al. |
| 8,052,636 B2 | 11/2011 | Moll et al. |
| 8,146,874 B2 | 4/2012 | Yu |
| 8,157,308 B2 | 4/2012 | Pedersen |
| 8,182,415 B2 | 5/2012 | Larkin et al. |
| 8,246,536 B2 | 8/2012 | Ochi |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,671,817 B1 | 3/2014 | Bogusky |
| 8,686,747 B2 | 4/2014 | Berner |
| 8,720,448 B2 | 5/2014 | Reis et al. |
| 8,746,252 B2 | 6/2014 | McGrogan et al. |
| 8,758,231 B2 | 6/2014 | Bunch et al. |
| 8,827,947 B2 | 9/2014 | Bosman et al. |
| 8,870,815 B2 | 10/2014 | Bhat et al. |
| 8,911,471 B2 | 12/2014 | Spiver et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,186,046 B2 | 11/2015 | Ramamurthy et al. |
| 9,204,933 B2 | 12/2015 | Reis et al. |
| 9,259,281 B2 | 2/2016 | Griffiths et al. |
| 9,314,306 B2 | 4/2016 | Yu |
| 9,314,953 B2 | 4/2016 | Lauer |
| 9,326,822 B2 | 5/2016 | Lewis et al. |
| 9,408,669 B2 | 8/2016 | Kokish et al. |
| 9,427,551 B2 | 8/2016 | Leeflang et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,566,201 B2 | 2/2017 | Yu |
| 9,591,990 B2 | 3/2017 | Chen et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,130,427 B2 | 11/2018 | Tanner et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,383,765 B2 | 8/2019 | Alvarez et al. |
| 10,524,866 B2 | 1/2020 | Srinivasan |
| 10,639,114 B2 | 5/2020 | Schuh |
| 10,667,875 B2 | 6/2020 | DeFonzo |
| 10,743,751 B2 | 8/2020 | Landey et al. |
| 10,751,140 B2 | 8/2020 | Wallace et al. |
| 10,765,487 B2 | 9/2020 | Ho |
| 2001/0004676 A1 | 6/2001 | Ouchi |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0036748 A1 | 2/2003 | Cooper et al. |
| 2003/0056561 A1 | 3/2003 | Butscher et al. |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0167623 A1 | 9/2003 | Lorenz |
| 2003/0195664 A1 | 10/2003 | Nowlin et al. |
| 2003/0212308 A1 | 11/2003 | Bendall |
| 2004/0015053 A1 | 1/2004 | Bieger |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0152972 A1 | 8/2004 | Hunter |
| 2004/0193013 A1 | 9/2004 | Isakawa et al. |
| 2004/0243147 A1 | 12/2004 | Lipow |
| 2004/0249246 A1 | 12/2004 | Campos |
| 2004/0254566 A1 | 12/2004 | Plicchi |
| 2005/0004515 A1 | 1/2005 | Hart et al. |
| 2005/0004579 A1 | 1/2005 | Schneider et al. |
| 2005/0125005 A1 | 6/2005 | Fujikura |
| 2005/0131279 A1 | 6/2005 | Boulais et al. |
| 2005/0154262 A1 | 7/2005 | Banik et al. |

(56) References Cited

U.S. PATENT DOCUMENTS

| | | |
|---|---|---|
| 2005/0159646 A1 | 7/2005 | Nordstrom et al. |
| 2005/0165366 A1 | 7/2005 | Brustad |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0041188 A1 | 2/2006 | Dirusso et al. |
| 2006/0041245 A1 | 2/2006 | Ferry |
| 2006/0111692 A1 | 5/2006 | Hlavka et al. |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0149946 A1 | 6/2007 | Viswanathan |
| 2007/0156019 A1 | 7/2007 | Larkin et al. |
| 2007/0185485 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147011 A1 | 6/2008 | Urmey |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0214925 A1 | 9/2008 | Wilson et al. |
| 2008/0218770 A1 | 9/2008 | Moll et al. |
| 2008/0243064 A1 | 10/2008 | Stahler et al. |
| 2008/0245946 A1 | 10/2008 | Yu |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0302200 A1 | 12/2008 | Tobey |
| 2009/0005768 A1 | 1/2009 | Sharareh |
| 2009/0082722 A1 | 3/2009 | Munger et al. |
| 2009/0098971 A1 | 4/2009 | Ho et al. |
| 2009/0099420 A1 | 4/2009 | Woodley et al. |
| 2009/0105645 A1 | 4/2009 | Kidd et al. |
| 2009/0163851 A1 | 6/2009 | Holloway |
| 2009/0163948 A1 | 6/2009 | Sunaoshi |
| 2009/0171371 A1 | 7/2009 | Nixon |
| 2009/0247880 A1 | 10/2009 | Naruse et al. |
| 2009/0247944 A1 | 10/2009 | Kirschenman et al. |
| 2009/0248039 A1 | 10/2009 | Cooper et al. |
| 2009/0254083 A1 | 10/2009 | Wallace et al. |
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0130923 A1 | 5/2010 | Cleary et al. |
| 2010/0130987 A1 | 5/2010 | Wenderow et al. |
| 2010/0168918 A1 | 7/2010 | Zhao |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0217184 A1 | 8/2010 | Koblish et al. |
| 2010/0248177 A1 | 9/2010 | Mangelberger et al. |
| 2010/0249497 A1 | 9/2010 | Peine et al. |
| 2010/0249506 A1 | 9/2010 | Prisco et al. |
| 2010/0274078 A1 | 10/2010 | Kim et al. |
| 2010/0332033 A1 | 12/2010 | Diolaiti |
| 2011/0009863 A1 | 1/2011 | Stanislaw |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0147030 A1 | 6/2011 | Blum et al. |
| 2011/0148442 A1 | 6/2011 | Berner |
| 2011/0152880 A1 | 6/2011 | Alvarez et al. |
| 2011/0238083 A1 | 9/2011 | Moll et al. |
| 2011/0245844 A1 | 10/2011 | Jinno et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0132018 A1 | 5/2012 | Tang |
| 2012/0136419 A1 | 5/2012 | Zarembo et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0190976 A1 | 7/2012 | Kleinstreuer |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0241576 A1 | 9/2012 | Yu |
| 2012/0259244 A1 | 10/2012 | Roberts et al. |
| 2012/0277730 A1 | 11/2012 | Salahieh |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0066335 A1 | 3/2013 | Barwinkel |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0197556 A1 | 8/2013 | Shelton et al. |
| 2013/0204124 A1 | 8/2013 | Duindam |
| 2013/0226151 A1 | 8/2013 | Suehara |
| 2013/0231678 A1 | 9/2013 | Wenderow |
| 2013/0303892 A1 | 11/2013 | Zhao |
| 2013/0304084 A1 | 11/2013 | Beira et al. |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0012288 A1 | 1/2014 | Darisse |
| 2014/0046313 A1 | 2/2014 | Pederson et al. |

(56) References Cited

U.S. PATENT DOCUMENTS

| | | |
|---|---|---|
| 2014/0066944 A1 | 3/2014 | Taylor et al. |
| 2014/0069437 A1* | 3/2014 | Reis .................. A61B 90/40 128/852 |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0200402 A1 | 7/2014 | Snoke et al. |
| 2014/0222019 A1 | 8/2014 | Brudnick |
| 2014/0235943 A1 | 8/2014 | Paris |
| 2014/0243849 A1 | 8/2014 | Saglam et al. |
| 2014/0251042 A1 | 9/2014 | Asselin et al. |
| 2014/0276233 A1 | 9/2014 | Murphy |
| 2014/0276389 A1 | 9/2014 | Walker |
| 2014/0276391 A1 | 9/2014 | Yu |
| 2014/0276394 A1 | 9/2014 | Wong et al. |
| 2014/0276594 A1 | 9/2014 | Tanner et al. |
| 2014/0276647 A1 | 9/2014 | Yu |
| 2014/0276935 A1 | 9/2014 | Yu |
| 2014/0276936 A1 | 9/2014 | Kokish et al. |
| 2014/0277333 A1 | 9/2014 | Lewis et al. |
| 2014/0277334 A1 | 9/2014 | Yu et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2015/0012134 A1 | 1/2015 | Robinson |
| 2015/0031950 A1 | 1/2015 | Drontle et al. |
| 2015/0032151 A1 | 1/2015 | Ishida et al. |
| 2015/0051592 A1 | 2/2015 | Kintz |
| 2015/0090063 A1 | 4/2015 | Lantermann et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0255782 A1 | 9/2015 | Kim et al. |
| 2015/0327939 A1 | 11/2015 | Kokish et al. |
| 2015/0374445 A1 | 12/2015 | Gombert et al. |
| 2016/0000414 A1 | 1/2016 | Brown |
| 2016/0000512 A1 | 1/2016 | Gombert et al. |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0100896 A1 | 4/2016 | Yu |
| 2016/0157945 A1 | 6/2016 | Madhani |
| 2016/0166234 A1 | 6/2016 | Zhang |
| 2016/0183841 A1 | 6/2016 | Duindam et al. |
| 2016/0192860 A1 | 7/2016 | Allenby |
| 2016/0206389 A1 | 7/2016 | Miller |
| 2016/0213435 A1 | 7/2016 | Hourtash |
| 2016/0227982 A1 | 8/2016 | Takahashi |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0281218 A1 | 10/2017 | Timm |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0325932 A1 | 11/2017 | Hoelzle |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0055589 A1 | 3/2018 | Joseph et al. |
| 2018/0056044 A1 | 3/2018 | Choi et al. |
| 2018/0104820 A1 | 4/2018 | Troy et al. |
| 2018/0116735 A1 | 5/2018 | Tierney et al. |
| 2018/0177556 A1 | 6/2018 | Noonan et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223967 A1 | 7/2019 | Abbott |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0231458 A1 | 8/2019 | DiMaio |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0336238 A1 | 11/2019 | Yu |
| 2019/0365209 A1 | 12/2019 | Ye et al. |

(56) References Cited

U.S. PATENT DOCUMENTS

| | | | |
|---|---|---|---|
| 2019/0365479 | A1 | 12/2019 | Rafii-Tari |
| 2019/0365486 | A1 | 12/2019 | Srinivasan et al. |
| 2019/0375383 | A1 | 12/2019 | Alvarez |
| 2019/0380787 | A1 | 12/2019 | Ye |
| 2020/0000533 | A1 | 1/2020 | Schuh |
| 2020/0008874 | A1 | 1/2020 | Barbagli et al. |
| 2020/0022767 | A1 | 1/2020 | Hill |
| 2020/0038128 | A1 | 2/2020 | Joseph |
| 2020/0039086 | A1 | 2/2020 | Meyer |
| 2020/0046434 | A1 | 2/2020 | Graetzel |
| 2020/0046942 | A1 | 2/2020 | Alvarez |
| 2020/0054408 | A1 | 2/2020 | Schuh et al. |
| 2020/0060516 | A1 | 2/2020 | Baez |
| 2020/0086087 | A1 | 3/2020 | Hart et al. |
| 2020/0091799 | A1 | 3/2020 | Covington et al. |
| 2020/0093549 | A1 | 3/2020 | Chin |
| 2020/0093554 | A1 | 3/2020 | Schuh |
| 2020/0100845 | A1 | 4/2020 | Julian |
| 2020/0100855 | A1 | 4/2020 | Leparmentier |
| 2020/0101264 | A1 | 4/2020 | Jiang |
| 2020/0107894 | A1 | 4/2020 | Wallace |
| 2020/0121502 | A1 | 4/2020 | Kintz |
| 2020/0129252 | A1 | 4/2020 | Kokish |
| 2020/0146769 | A1 | 5/2020 | Eyre |
| 2020/0155245 | A1 | 5/2020 | Yu |
| 2020/0155801 | A1 | 5/2020 | Kokish |
| 2020/0188043 | A1 | 6/2020 | Yu |
| 2020/0197112 | A1 | 6/2020 | Chin |
| 2020/0206472 | A1 | 7/2020 | Ma |
| 2020/0217733 | A1 | 7/2020 | Lin |
| 2020/0222134 | A1 | 7/2020 | Schuh |
| 2020/0230360 | A1 | 7/2020 | Yu |
| 2020/0237458 | A1 | 7/2020 | DeFonzo |
| 2020/0261172 | A1 | 8/2020 | Romo |
| 2020/0268459 | A1 | 8/2020 | Noonan et al. |
| 2020/0268460 | A1 | 8/2020 | Tse |

FOREIGN PATENT DOCUMENTS

| | | |
|---|---|---|
| CN | 101161426 | 4/2008 |
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102711586 | 10/2012 |
| CN | 102834043 | 12/2012 |
| CN | 102973317 | 3/2013 |
| CN | 102015759 | 4/2013 |
| CN | 103735313 | 4/2014 |
| CN | 103767659 | 5/2014 |
| CN | 103930063 | 7/2014 |
| CN | 105147393 | 12/2015 |
| CN | 105559850 | 5/2016 |
| CN | 105559886 | 5/2016 |
| DE | 19649082 | 1/1998 |
| DE | 102004020465 | 9/2005 |
| EP | 0 543 539 | 5/1993 |
| EP | 0 776 739 | 6/1997 |
| EP | 1 442 720 | 8/2004 |
| EP | 0 904 796 | 11/2004 |
| EP | 2 567 670 | 3/2013 |
| EP | 3 025 630 | 6/2016 |
| JP | 07-136173 | 5/1995 |
| JP | 2006-525087 | 11/2006 |
| JP | 2007-511247 | 5/2007 |
| JP | 2009-139187 | 6/2009 |
| JP | 2010-046384 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/74178 | 9/2002 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 09/097461 | 6/2007 |
| WO | WO 07/146987 | 12/2007 |
| WO | WO 08/097540 | 8/2008 |
| WO | WO 09/092059 | 7/2009 |
| WO | WO 10/081187 | 7/2010 |
| WO | WO 11/005335 | 1/2011 |
| WO | WO 12/037506 | 3/2012 |
| WO | WO 13/107468 | 7/2013 |
| WO | WO 13/179600 | 12/2013 |
| WO | WO 15/093602 | 12/2013 |
| WO | WO 15/127231 | 8/2015 |
| WO | WO 16/003052 | 1/2016 |
| WO | WO 17/059412 | 4/2017 |
| WO | WO 17/0151993 | 9/2017 |

\* cited by examiner

MEDICAL INSTRUMENT HAVING TRANSLATABLE SPOOL

CROSS-REFERENCE

This application is a continuation of U.S. patent application Ser. No. 15/388,955, filed Dec. 22, 2016, which is a continuation of U.S. patent application Ser. No. 15/072,072, filed Mar. 16, 2016, which claims the benefit of U.S. Provisional Application No. 62/134,366, filed Mar. 17, 2015, which applications are incorporated herein by reference.

The present application relates to medical instruments, tools, and methods that may be incorporated into a robotic system, such as those disclosed in U.S. patent application Ser. No. 14/523,760, filed Oct. 24, 2014, U.S. Provisional Patent Application No. 62/019,816, filed Jul. 1, 2014, U.S. Provisional Patent Application No. 62/037,520, filed Aug. 14, 2014, and U.S. Provisional Patent Application No. 62/057,936, filed Sep. 30, 2014, the entire contents of which are incorporated herein by reference.

BACKGROUND

1. Field

The field of the present application relates to medical instruments that may be used in a number of procedures. More particularly, the field of the present application pertains to medical instruments having a translatable spool for use during endolumenal procedures.

2. Description of the Background Art

The spread of robotic surgery has precipitated the development of novel technologies. For example, in order to enable robotically-driven endoscopes, robotically-driven tools are more useful when they are able to both articulate in a desired linear direction and roll in a desired angular direction. In current elongated medical devices, roll in the device shafts is often achieved at the expense of pull-cable management. For example, in some laparoscopic devices on the market, roll of the rigid shaft may be accomplished by simply twisting the actuation pull wires (used for manipulation of the device's end effectors and/or wrist) around each other at the same rate as the shaft. Due to mechanically-limited revolutions in either direction, the twist in the cables show little to no adverse effect on either roll or grasper manipulation. Nevertheless, this lack of pull-wire management results in noticeably varying levels of friction throughout the shaft rotations. The accumulated friction steadily increases with each rotation until the pull wires are tightly bound around one another.

FIG. 1 illustrates the physical limitations of current elongated devices arising from the implementation of roll capabilities. Specifically, FIG. 1 illustrates how the implementation of roll capabilities in a prior art device creates undesirable friction and winding of the articulation pull wires. As shown in FIG. 1, the pull wires 104 in prior art device 100 extend from the distal tip 102 and at the proximal end 101 of the device 100. Rotation of the shaft 103 forces the pull wires 104 to twist amongst one another along the entire length of the hollow shaft 103. As the shaft 103 rotates beyond a full rotation, the tensioned wires start to tightly wrap around one another much like a wire-rope. Eventually, the pull-wires 104 would not be able to overcome the resulting friction to exert tension on the elements on the distal end 102.

In competing products, such as the TransEnterix Surg-iBot, articulation and roll are de-coupled using a robotic outer "sheath" to enable pitch and yaw articulation, while a flexible laparoscopic tool controls insertion roll and end-effector actuation. However, this results in an unnecessarily large system with two separate modules controlling different degrees of freedom. Separate modules complicate the pre-operative workflow because the operator must now register two sets of devices relative to the patient.

In manual endoscopes, knobs and dials actuate the distal tip of the scope while rotation of the shaft is achieved by twisting the entire proximal end of the tool. As a result, when rolling the scope, the operator is forced to contort into an uncomfortable, compensatory position in order to operate the knobs and dials. These contortions are undesirable; thus, necessitating a different approach.

Accordingly, there is a need for an endoscopic tool that is capable of rolling without compromise to its actuation and articulation capabilities, while also being ergonomically ease to use.

SUMMARY

In general, the present application relates to a medical instrument configured for use with a robotic system, the medical instrument comprising: an instrument base configured to couple to a robotic drive mechanism of the robotic system; an elongate shaft coupled to the instrument base, the elongate shaft having a distal end; a pull wire fixedly coupled to the distal end of the elongate shaft, the pull wire being configured to actuate the elongate shaft; and a rotatable spool in the instrument base, the rotatable spool being configured to direct the pull wire to the elongate shaft at an angle, wherein the rotatable spool is configured to translate in coordination with actuation of the elongate shaft to control the angle of the pull wire relative to the elongate shaft.

In another aspect, there is provided a medical robotic system comprising: a medical instrument comprising an elongate shaft, a rotatable spool, and a pull wire arranged around the rotatable spool and fixedly coupled to the elongate shaft, wherein the pull wire exits the rotatable spool at an angle; and a robotic drive mechanism coupled to the medical instrument, the robotic drive mechanism being configured to actuate the elongate shaft by applying tension to the pull wire, wherein the robotic drive mechanism is further configured to control the angle of the pull wire by translating the rotatable spool in coordination with applying the tension to the pull wire.

In yet another aspect, there is provided a medical instrument configured for use with a robotic system, the medical instrument comprising: an elongate shaft configured to be inserted into an anatomy of a patient; a pull wire coupled to the elongate member; a robotic interface coupled to the pull wire, the robotic interface being configured to exert a pulling force on the pull wire to control a degree of freedom of the elongate member; and a redirect member configured to translate simultaneously with exertion of the pulling force on the pull wire, wherein the pull wire is routed around the redirect member so that is exits the redirect member at an angle, and wherein translation of the redirect member maintains the angle at which the pull wire exits the redirect member.

BRIEF DESCRIPTION OF THE DRAWINGS

The invention will be described, by way of example, and with reference to the accompanying diagrammatic drawings, in which.

DETAILED DESCRIPTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

In clinical applications, the design of the instrument base, which includes the robotic interface and the mechanical assembly to enable articulation and roll, is often constrained in size and design. For example, in a robotically-driven system, the design of the instrument base may be limited by both the lifting power of the robotic appendages and the necessity of maintaining a sterile barrier. Moreover, the use of pull wires to actuate the endoscopic shaft further complicates attempts to implement roll into the endoscopic shaft design.

Accordingly, the present application describes an efficient, compact design for a robotically-driven tool that accomplishes both articulation and roll in its shaft with minimal design compromises.

Figure 1:
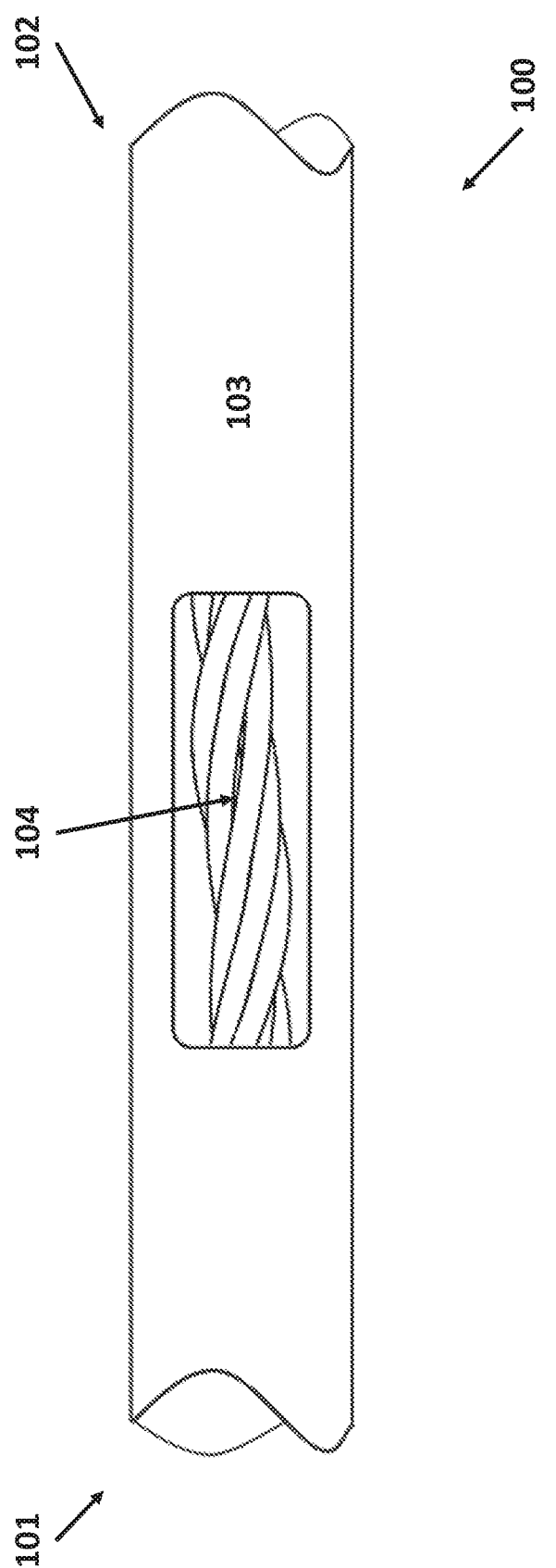
FIG. 1 illustrates the physical limitations in current elongated devices arising from the implementation of roll capabilities, consistent with the current state of the art.
Figure 2A:
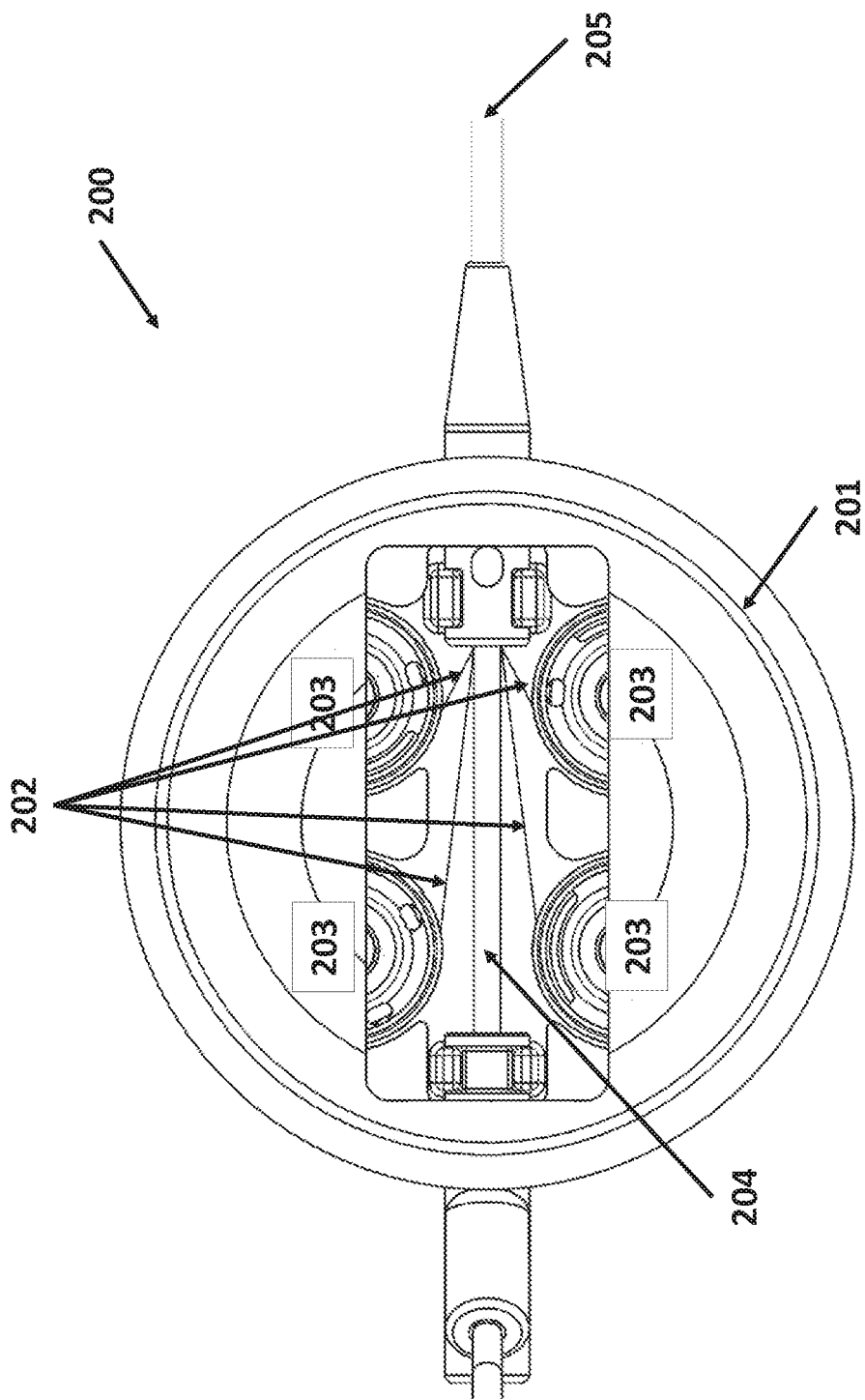
FIGS. 2A-2C illustrates the physical limitations arising from use of a central shaft to capture the winding pull wires arising from rotations, in accordance with an embodiment of the present invention.
Figure 2B:
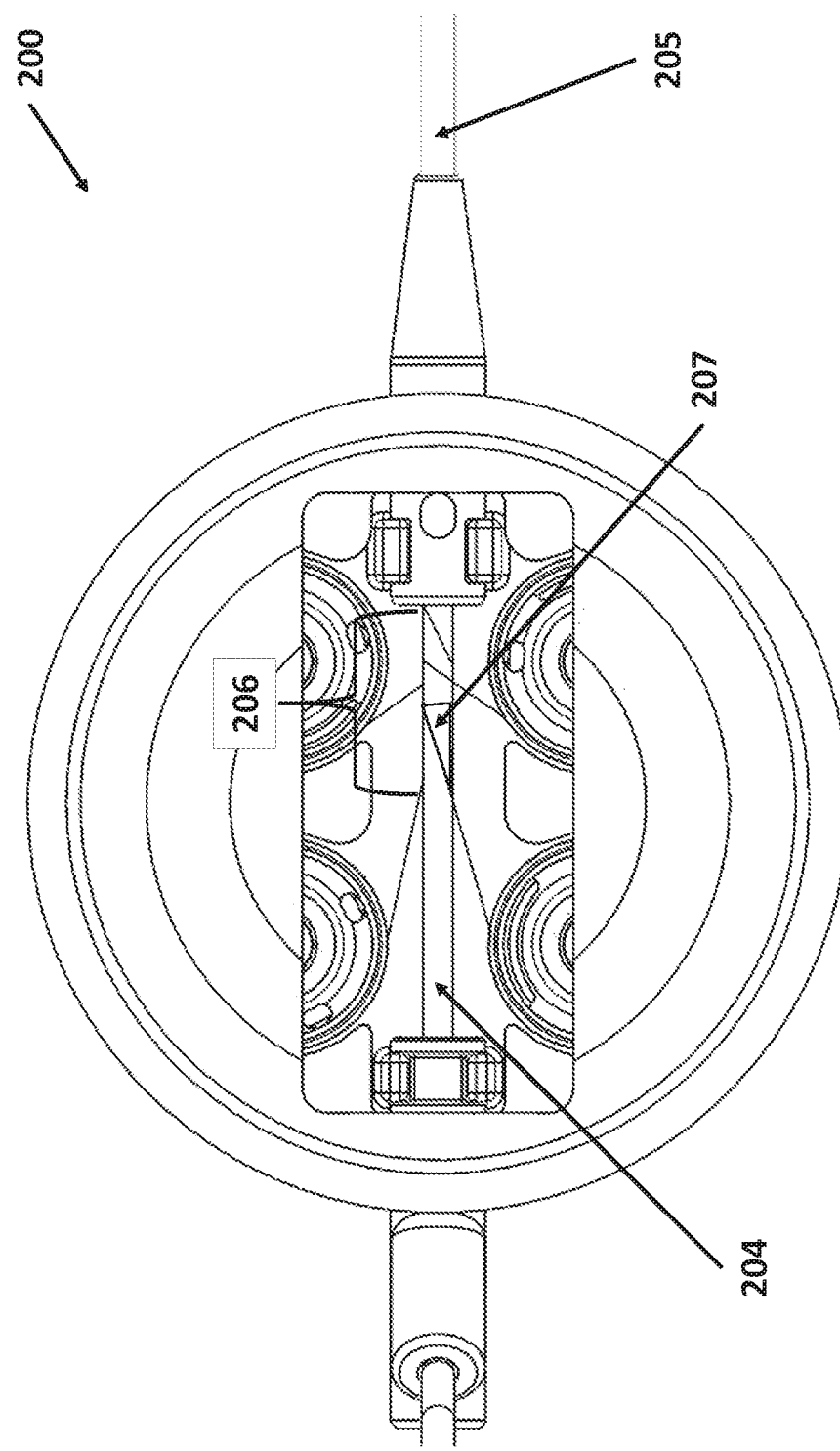
Figure 2C:
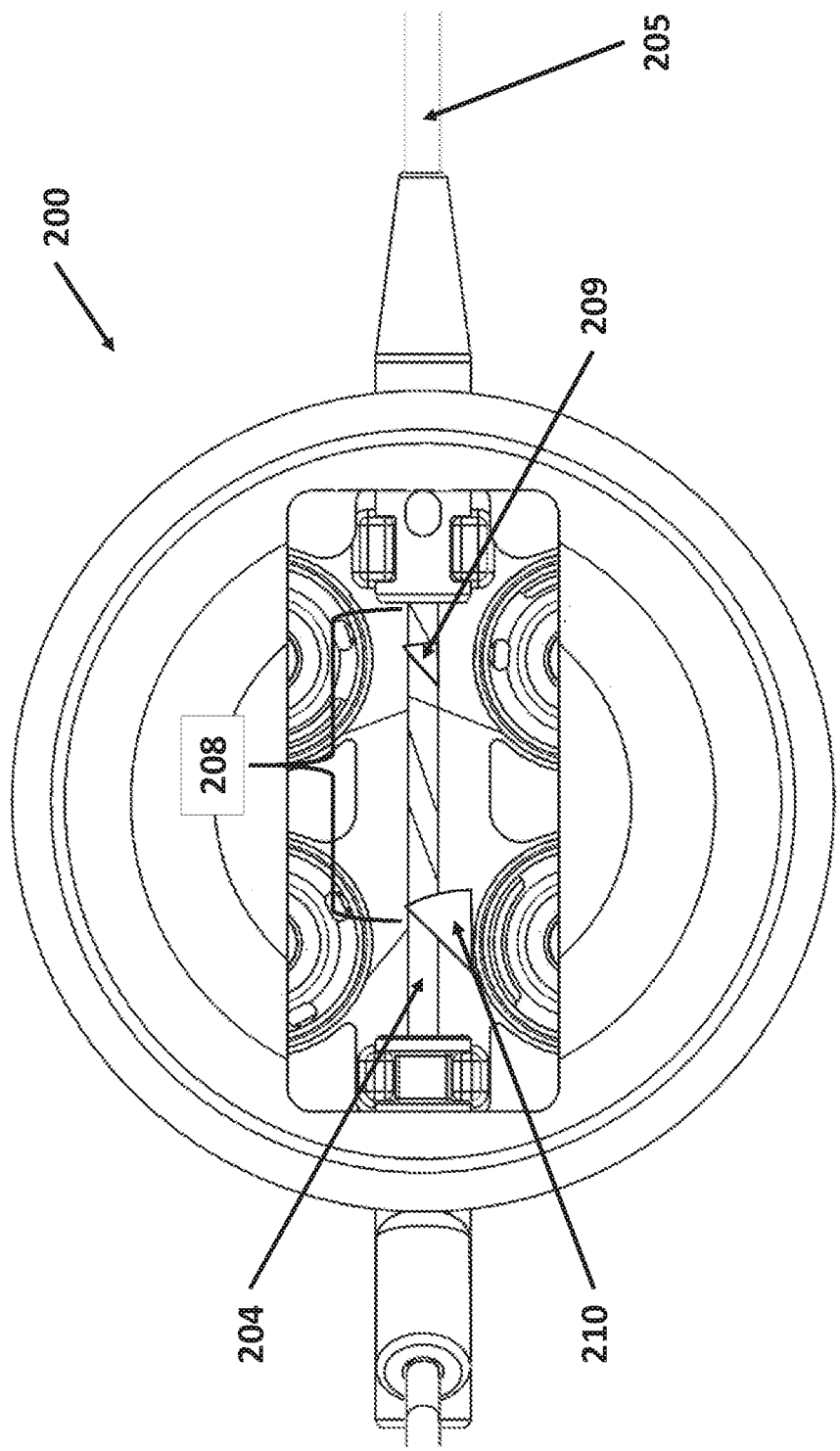

An improvement on current devices, use of an internal shaft within the elongated shaft may be used to interrupt the wire-on-wire wrapping by introducing a low-friction surface upon which the wire can wrap around. Merely adding an internal shaft to the current art, however, creates a number of engineering challenges. FIGS. 2A-2C illustrates the physical limitations arising from use of a central shaft to capture the winding pull wires arising from rotations, in accordance with an embodiment of the present invention. In FIG. 2A, the device 200 remains at rest with respect to roll, revealing that the pull wires 202 within the instrument base 201 in device 200 extend from the spools 203 to the distal end of the internal shaft 204. The outer shaft 205 is configured with a concentrically aligned internal shaft 204 that is designed to act as a low-friction surface upon which the wires may wrap around.

In FIG. 2B, the outer shaft 205 has been slightly rotated, resulting in the pull wires 202 winding around the internal shaft 204. The pull wire 202 winding and twisting around internal shaft 204 results in the pull wires 202 spiraling into a wrap 206 around the internal shaft 204 at particular helical angle 207 and helical pitch as the outer shaft 205 rolls.

In FIG. 2C, the outer shaft 205 has been heavily rotated, resulting the pull wires 202 further winding around the internal shaft 204. As the outer shaft 205 is rotated, the pull wires 202 "crawl" along the internal shaft 204 in order to compensate for their changed angular position with respect to the internal shaft 204. The resulting wrap 208 of the pull wires 202, however, causes the helical angle 209 of the wrap 208 to grow progressively aggressive, i.e., the helical angles of the wrap 208 grow steeper and steeper relative to the internal shaft 204.

The change in the helical angles of wrap 208 are largely the result of the changing "takeoff angle" 210, i.e., the angle at which the pull wires 202 begin to wrap around the internal shaft 204, as the external shaft 205 rolls. As the internal shaft 204 rotates, the static position of the spools 202 relative to internal shaft 204 and wrap 208 creates a steeper and steeper takeoff angle 210 as the wrap 208 crawls along the internal shaft 204. Additionally, since the spools are at different locations relative to the wrap 208, the takeoff angles at each spool may be different. At the extreme, the wrap 208 around the internal shaft 204 would lock due to friction, a phenomenon that reflects Capstan's principle, wherein the helical pitch 209 would be orthogonal to the internal shaft 204, resulting in the wrap 208 completely wrapping about itself, i.e., where the helical pitch would be zero. At that point, the pull-wire 202 would not be able to overcome the friction and serve its purpose.

The "crawl" of the wrap 208 also transmits tension in the pull wires 202. When pull wires are used in flexible devices, such as catheters, the resulting tension from roll is undesirable and can lead to shaft compression, unwanted stiffness, and hindered steering performance. Moreover, the resulting tension is non-linear and unpredictable, leading to an unpredictable mathematical model for controlling the device. Given that a changing helical angle and helical pitch creates controls and engineering challenges, additional embodiments are needed that incorporate internal shaft roll mechanisms to accommodate.

Figure 3:
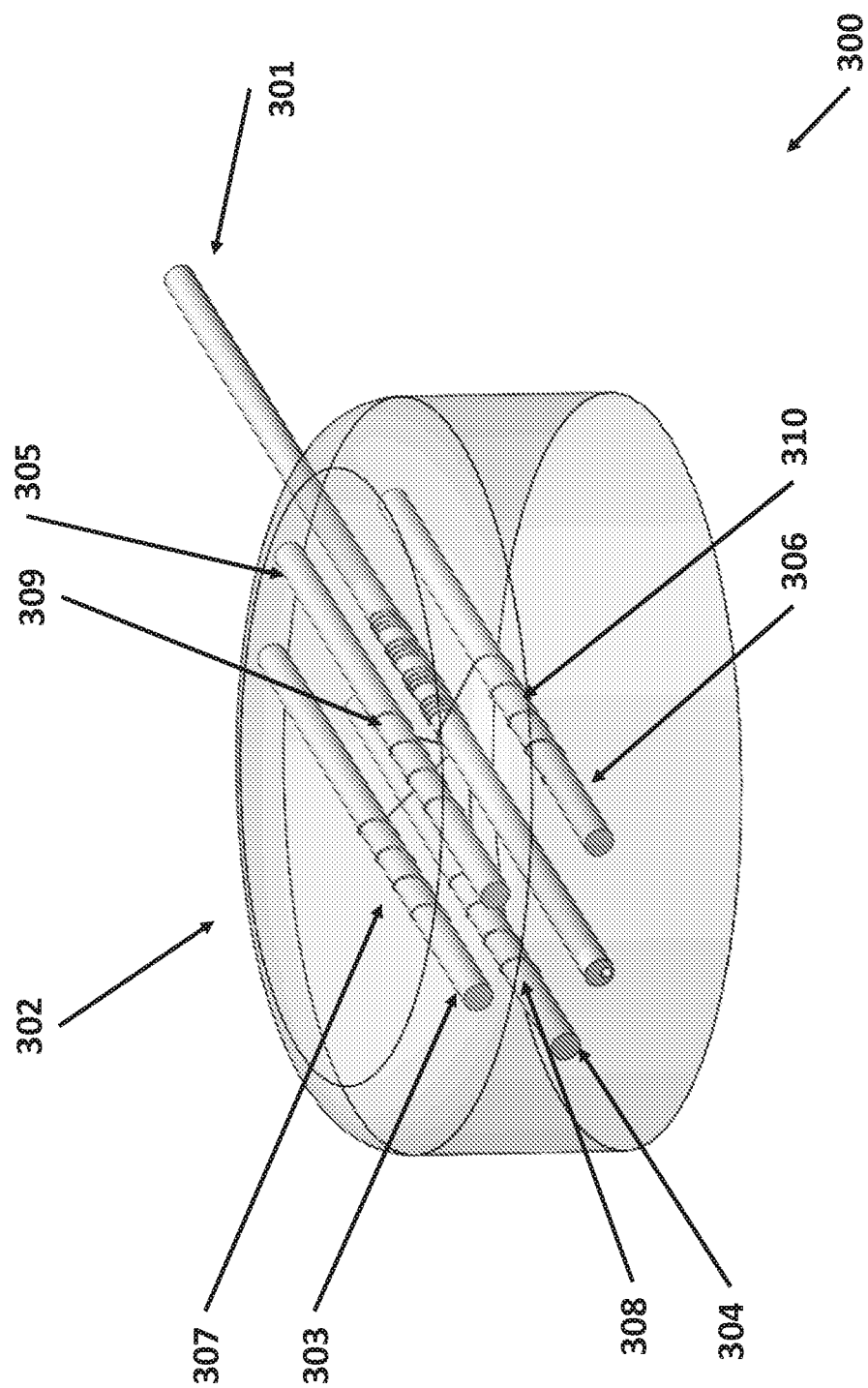
FIG. 3 illustrates an endoscopic device with an instrument base comprising multiple rolling structures, in accordance with an embodiment of the present invention.

FIG. 3 illustrates an endoscopic device with an instrument base comprising multiple rolling structures, in accordance with an embodiment of the present invention. In FIG. 3, the device 300 comprises an elongated shaft 301 and instrument base 302. The instrument base 302 comprises four articulation shafts 303, 304, 305, and 306 that act as redirect surfaces for pull wires 307, 308, 309, and 310 respectively. Each of the aforementioned pull wires are wrapped in spiral fashion around their respective articulation shafts before being wrapped in spiral fashion around the elongated shaft 301.

Figure 4A:
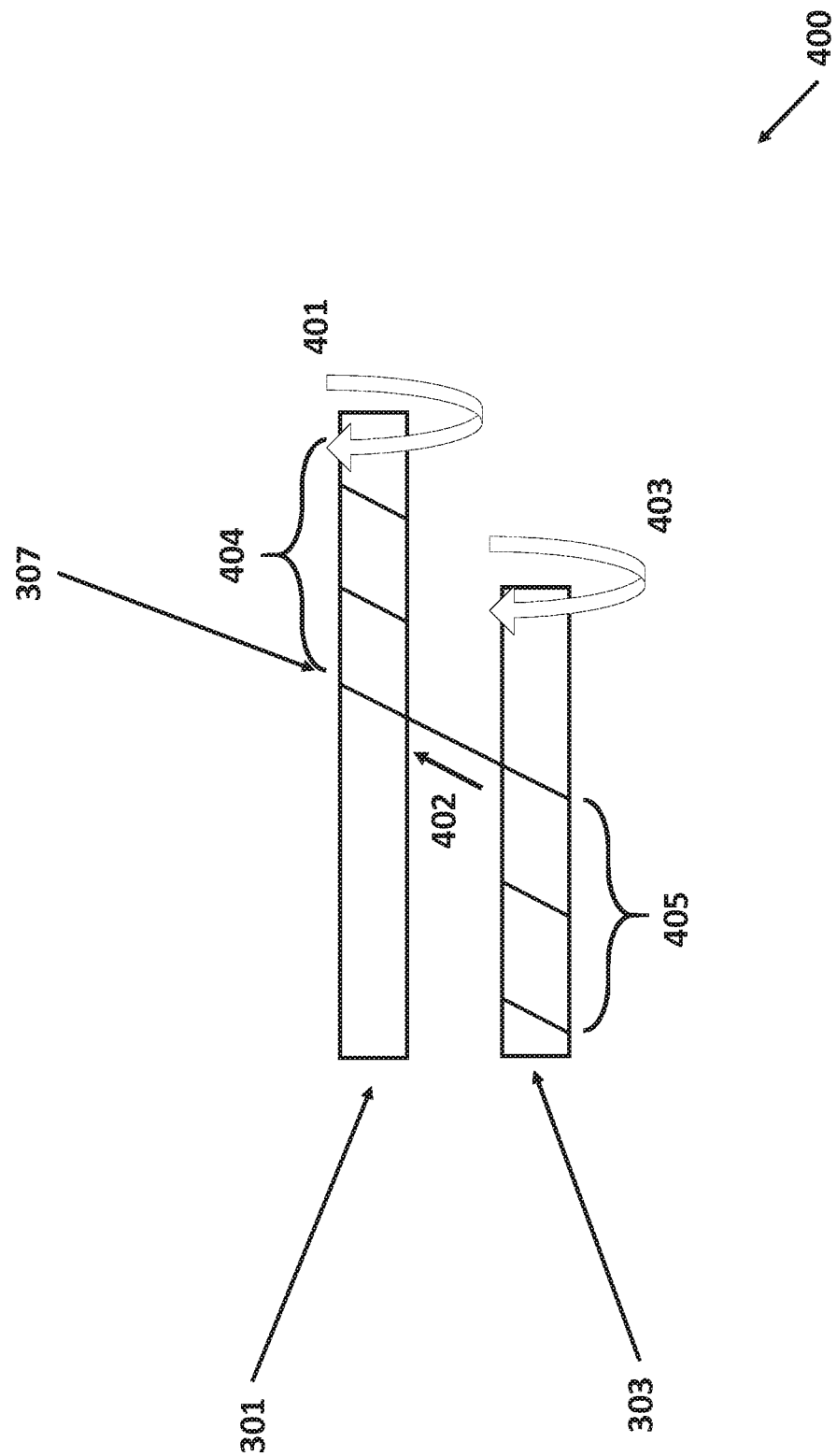
FIGS. 4A-4B illustrates how the helical angle of the pull wire wrap around the elongated shaft may be controlled by rolling the articulation shaft in concert with rolling the elongated shaft, in accordance with an embodiment of the present invention.
Figure 4B:
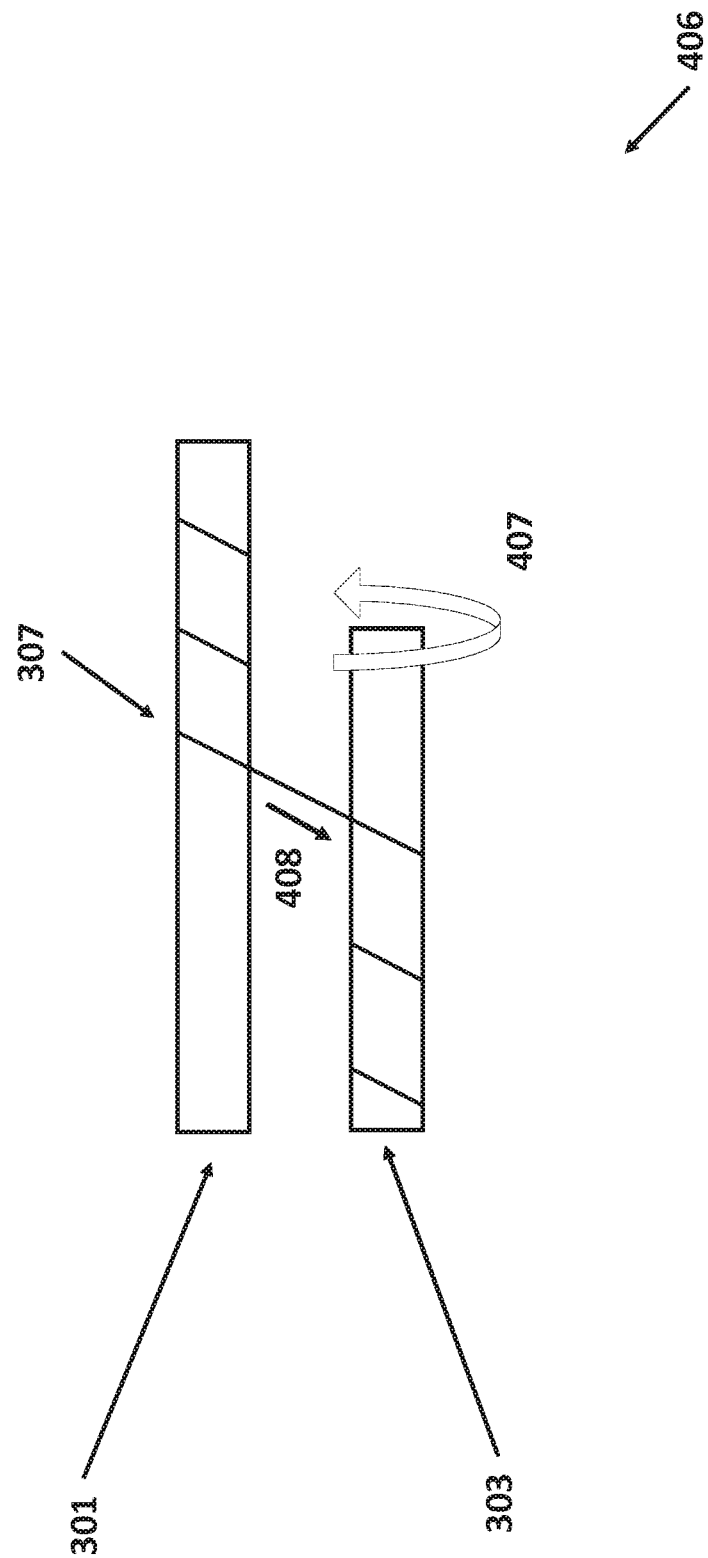

The use of parallel articulation shafts provides for controlled wrapping of the pull wires around the elongated shaft due to roll by coordinating roll among the articulation shafts. FIGS. 4A-4B illustrates how the helical angle of the pull wire wrap around the elongated shaft may be controlled by rolling the articulation shaft in concert with rolling the elongated shaft, in accordance with an embodiment of the present invention. Specifically, FIG. 4A illustrates how roll of the elongated shaft 301 from device 300 may be accomplished without creating an unstable helical pitch and angle and undesirable tension. In FIG. 4A, view 400 isolates and focuses on pull wire 307 wrapped around both articulation shaft 303 and elongated shaft 301 within instrument base 302 of device 300 from FIG. 3. When elongated shaft 301 is rolled in the direction shown by arrow 401, in the absence of any corresponding roll in articulation shaft 303, undesirable tension 402 would result in pull wire 307. Accordingly, to compensate for that rise in tension 402, articulation shaft 303 may be rolled in the (same) direction as the elongated shaft 301 as shown by arrow 403. In effect, as the elongated shaft 301 "wraps" up the pull wire 307, additional length of pull wire 307 is "unwrapped" from articulation shaft 303. When the rate of roll 401 and 403 are matched, there is no tension or slack in the pull wire 307. This ensures that the helical pitch and angle of the wrap 404 on elongated shaft 301 and the helical pitch and angle of the wrap 405 on the articulation shaft 303 is consistent and predictable. This results in a linear mathematical model for calculating control of the pull wire 307.

FIG. 4B illustrates how tension on pull wire 307 may be generated by rolling the articulation shaft 303 relative to the elongated shaft 301, in accordance with an embodiment of the present invention. In FIG. 4B, view 406 shows rotation of the articulation shaft 303 in the direction indicated by arrow 407. If elongated shaft 301 rolls at a slower rate in the same direction, rolls in the opposite direction, or is held in place rotationally, pull wire 307 will experience tension in the direction indicated by arrow 408. Accordingly, tension along the pull wire 307 conveys axial compression force down the elongated shaft 301 of the device, resulting in articulation of the device. In circumstances when used in combination with an end effector, the axial compression results in actuation of the end effector element.

As shown in FIGS. 4A and 4B, providing secondary structures that assist with the wrap may accommodate the wrapping of the pull wires around the central shaft. The coordinated rolling of both the elongated shaft 301 in combination with the articulation shaft 303, which wraps pull wires at a precise helical pitch and angle, allows for a consistent helical pitch and angle on the elongated shaft 301, regardless of whether the operator desires roll in the elongated shaft 301 or tension in the pull wires. In practice, maintaining a consistent helical pitch generally results in a consistent helical angle.

While embodiments with multiple rolling structures resolve several of the design challenges arising from incorporating articulation and roll, in practice, the use of multiple rolling structures may create issues when attempting to interface the instrument with the robotic drive mechanism.

Figure 5A:
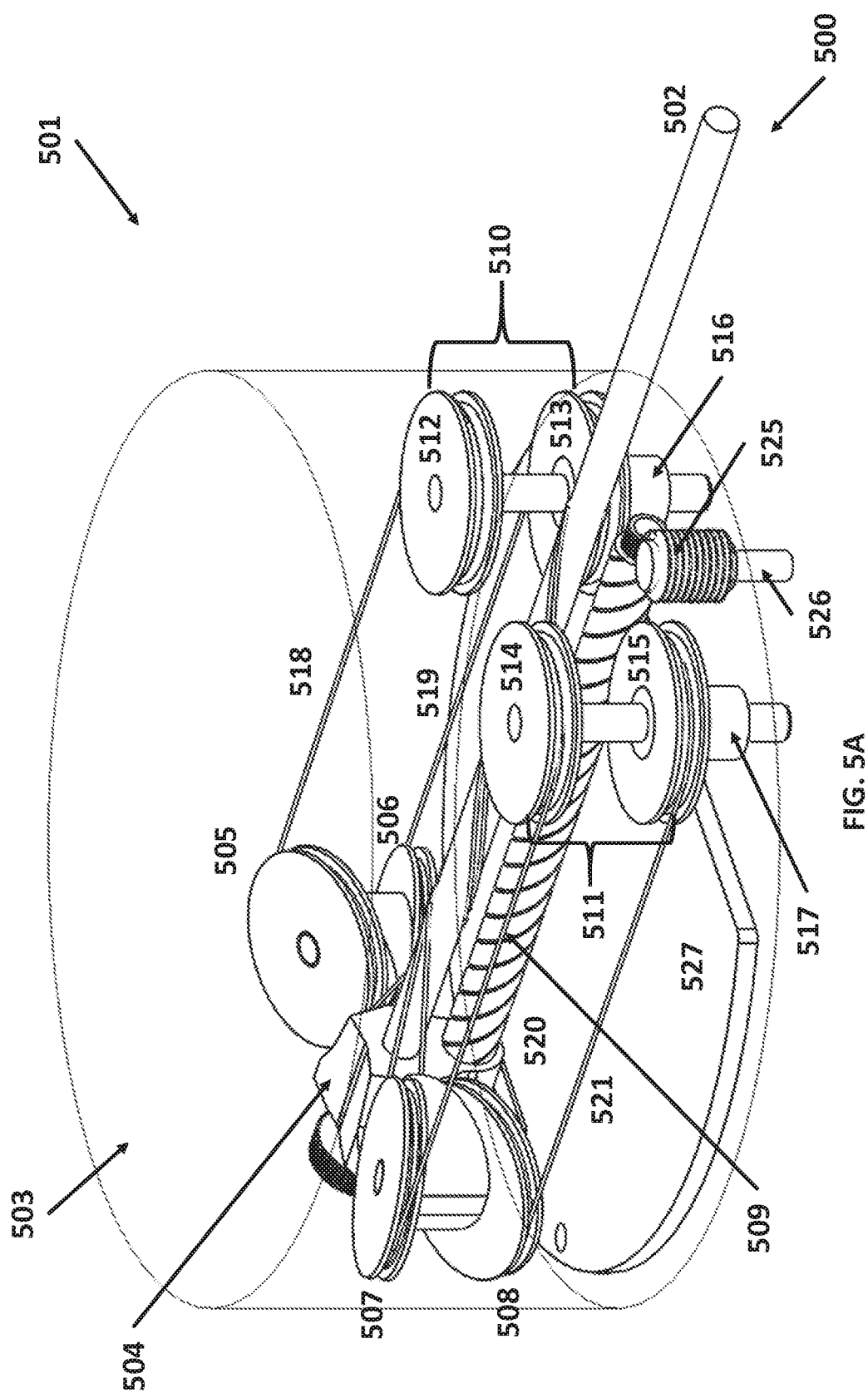
FIG. 5A illustrates an endoscopic device with an instrument base that utilizes a lead screw and angled idlers to ensure a consistent helical pitch around an elongated shaft, in accordance with an embodiment of the present invention.

FIG. 5A illustrates an endoscopic device with an instrument base that utilizes a lead screw and angled idlers to ensure a consistent helical angle and pitch around an elongated shaft, in accordance with an embodiment of the present invention. As shown in isometric transparent view 500, endoscopic device 501 principally comprises an elongated shaft 502 and an instrument base 503. Within instrument base 503, an idler carriage 504 is disposed along the elongated shaft 502, and configured to longitudinally translate and slide along the elongated shaft 502.

Figure 5B:
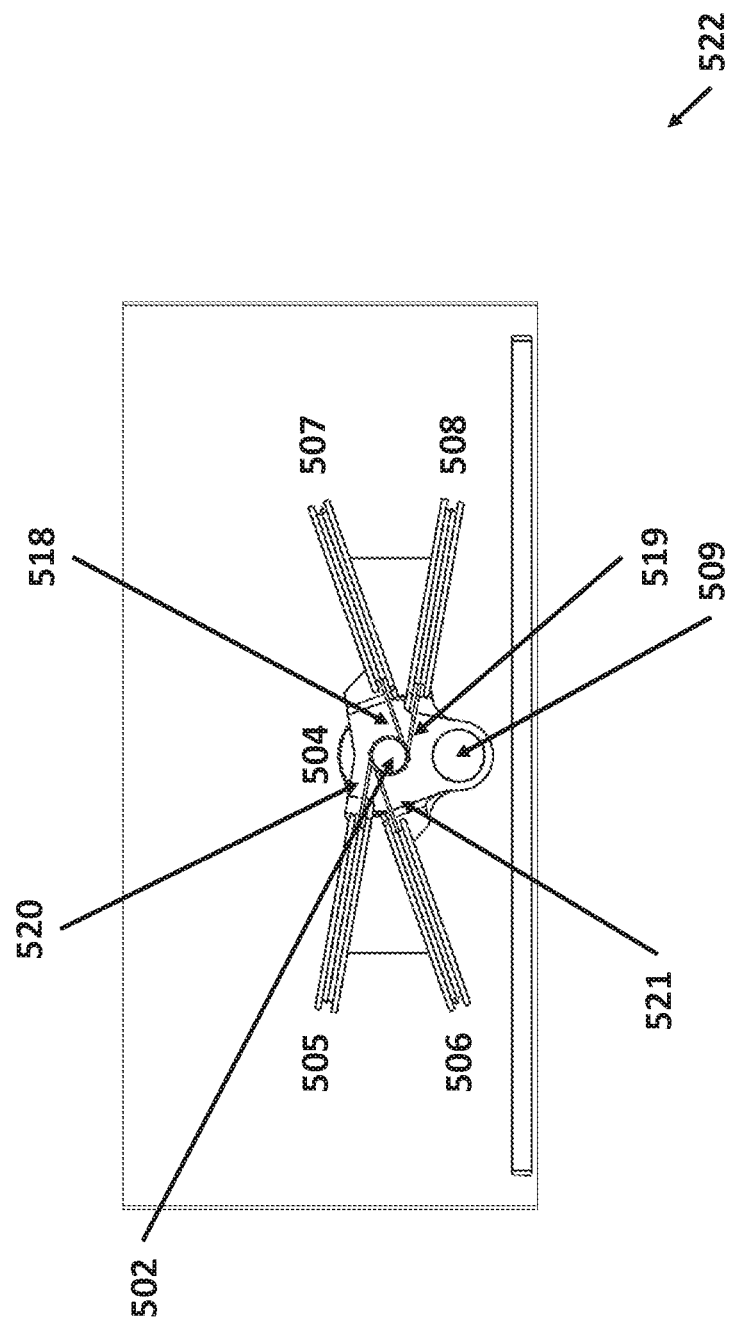
FIG. 5B illustrates a frontal view of idler carriage 504 and elongated shaft 502 in endoscopic device 501 from FIG. 5A.

The idler carriage 504 holds four angled idlers 505, 506, 507, and 508 at a fixed angle relative to the elongated shaft 502. The angle of the angled idlers may be chosen for a particular purpose. FIG. 5B illustrates a frontal view of idler carriage 504 and elongated shaft 502 in endoscopic device 501 from FIG. 5A. In FIG. 5B, cross-sectional frontal view 522 shows how the idler carriage 504 positions angled idlers 505, 506, 507, and 508 deliver the pull wires 518, 519, 520, and 521 to the elongated shaft 502 at a consistent and predictable location. In contrast to the previously disclosed embodiments, the angled idlers in endoscopic device 501 wrap and un-wrap the pull wires at the same longitudinal position along the elongated shaft 502, which assists in maintaining a consistent takeoff angle for all of the pull wires regardless of the length of pull wire wrap around shaft 502.

As shown in FIG. 5A, the instrument base 503 also incorporates a pair of rotating structures 510 and 511. Rotating structures 510 and 511 comprise two concentrically-aligned, co-radial spools, such as spools 512, 513 from rotating structure 510, and spools 514, 515 from rotating structure 511. The rotating structures 510 and 511 incorporate output shafts 516 and 517 that interface with robotic drive and control mechanisms. Given that spools 512 and 513 and spools 514 and 515 are co-radial, output shaft 516 and 517 each includes both an inner and outer sub-shaft that drives each spool per rotating structure.

In some embodiments, the output shafts may be replaced by "female" or receiving interfaces rather "male" or protruding interfaces. As shown in isometric view 500, pull wires 518, 519, 520, and 521 are coiled around spools 512, 513, 514, and 515 and run around the angled idlers 505, 506, 507, and 508 before spiraling around the elongated shaft 502.

Figure 5C:
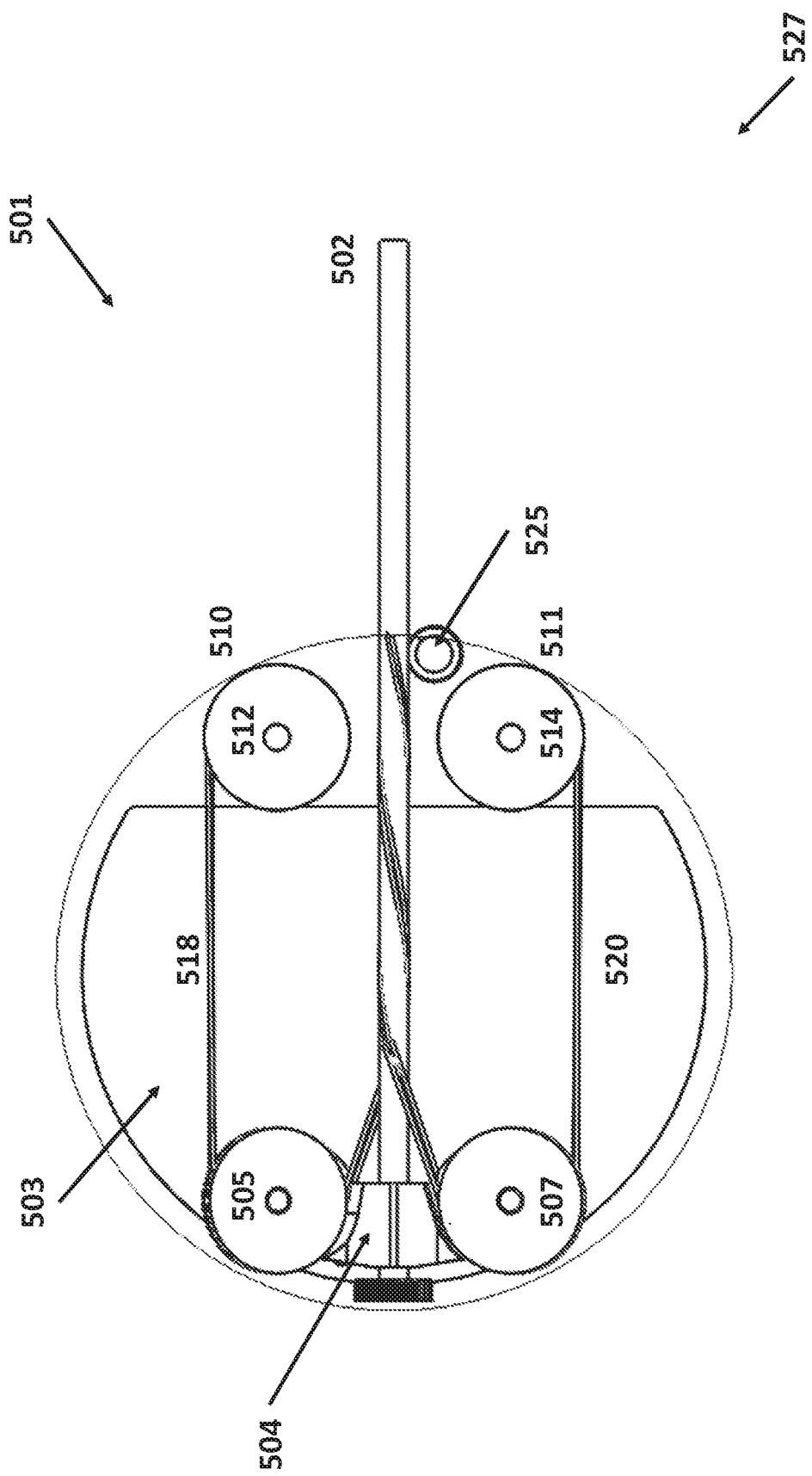
FIG. 5C illustrates a top view that shows the configuration of the key components of endoscopic device 501 from FIG. 5A.

FIG. 5C illustrates a top view that shows the configuration of the key components of endoscopic device 501 from FIG. 5A. Specifically, top view 527 provides a view of the direct alignment of a tangential path between rotation structures 510 and 511 and angled idlers 505 and 507 on idler carriage 504. As shown in top view 527, pull wire 518 is coiled around spool 512 and fed around angled idler 505 before spiraling around elongated shaft 502. The tangential path of the pull wires 518, 520 around the idlers 505, 507 are aligned with the spools 512, 514. Thus, in some embodiments, the spools 513 and 515 are also aligned with the angled idlers 506 and 508 in order for pull wires 519 and 521 to have a direct transmission path between the spools and idlers. In some embodiments, the idlers 505, 506, 507, and 508 may rotate in order to reduce friction as the pull wires 518, 519, 520, and 521 wind around them. While the idlers 505, 506, 507, and 508 operate similar to rotatable spools or pulleys, other embodiments may use other types of redirect members, such as surfaces.

Maintaining a consistent wrapping and unwrapping position and takeoff angle helps ensure that the pull wires spiral around the elongated shaft 502 at a consistent helical pitch. The consistency in the helical pitch greatly increases the ability of the robotic system to control and predict the tension on the pull wires.

In some embodiments, the elongated shaft 502 may be fixedly coupled to a concentric internal shaft that solely resides within the instrument base and is designed for wrapping pull wires around itself. Rolling the internal shaft would effectively roll the elongated shaft while potentially providing other advantages. For example, a distinct internal shaft may be adopted in order to take advantage of different coefficients of friction, different pull wire guiding features, such as grooves or lumens, different diameters, and potentially reduced manufacturing complexity and/or costs.

Angular motion from the robotic interface may create, for example, rotational motion in spool 512 through output shaft 516. Rotational motion in spool 512 may then exert compressive tension in pull wire 518. Tension in pull wire 518 may be carried around angled idler 505 and exerted on the pull wire 518 as it wraps onto elongated shaft 502. Where the pull wires 518 are fixedly coupled to the distal end of the shaft 502, the transmission of the compressive tension along pull wire 518 may then articulate the shaft 502. Thus, the angular motion in the robotic interface may generate articulation in shaft 502.

The instrument base 503 also comprises a lead screw 509 that runs parallel to the elongated shaft 502. Rotation of lead screw 509 is operated by a right angle gear transmission 525, which is visible in isometric view 500 from FIG. 5A. Rotational force in right angle gear transmission 525 originates from lead screw output shaft 526 which interfaces with external robotic drive and control mechanisms. Thus, angular motion in the robotic interface may rotate lead screw output shaft 526 to generate angular motion that ultimately rotates lead screw 509. As with the rotational structures 510 and 511, rotation motion from the robotic interface may also be transmitted to right angle gear transmission 525 using "female" or receiving connectors, rather than lead screw output shaft 526, which is considered a "male" connector.

Figure 5D:
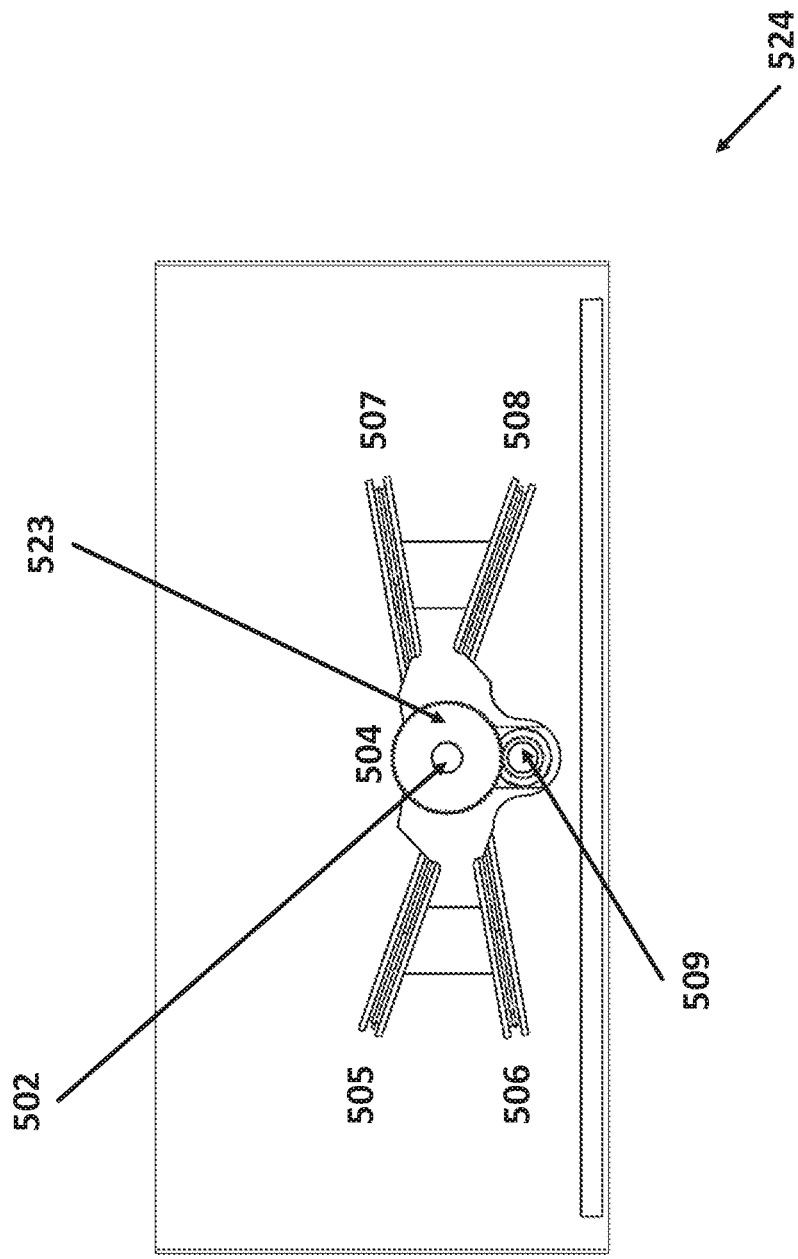
FIG. 5D illustrates a rear view of the elongated shaft idler carriage FIGS. 5A, 5B and 5C.

FIG. 5D illustrates a rear view of the elongated shaft and idler carriage from FIGS. 5A, 5B, and 5C. As shown in rear view 524 from FIG. 5D, lead screw 509 is operatively coupled to elongated shaft 502 through a shaft transmission gear 523. Shaft transmission gear 525 transmits angular motion from the lead screw 509 that rotates the shaft 502. In different embodiments, the shaft transmission gear 523 may be selected from various gear and transmission ratios to ensure the desired rotational motion in the elongated shaft 502 relative to the lead screw 509.

The combination of the shaft 502, lead screw 509, and the idler carriage 504 manages the linear translation of the idler carriage 504 (and thus angled idlers 505, 506, 507, and 508) that helps preserve the helical pitch of the pull wires when rolling of shaft 502. In practice, elongated shaft 502 rotates at a relative speed determined by the angular motion transmitted by shaft transmission gear 523 which is proportional to the rotation of lead screw 509. As the lead screw 509 rotates itself and the elongated shaft 502, the idler carriage 504 acts as a nut on lead screw 509. This "lead screw nut" engagement advances the idler carriage 504 at a rate proportional to the rotation of both the lead screw 509 and elongated shaft 502. Thus, idler carriage 504 translates along the lead screw 509 while sliding freely along the elongated shaft 502 as lead screw 509 rotates itself and elongated shaft 502. The pitch and angle of the thread on lead screw 509 determines the direction and speed at which the idler carriage 504 advances relative to the elongated shaft 502. Similarly, the rate of rotation of elongated shaft 502 is dependent on at least the size of shaft transmission gear 523. Accordingly, careful calibration and selection of those components ensures that they properly coordinate in unison in order to keep consistent the helical pitch and angle of the pull wires about the elongated shaft 502.

Given that the idler carriage 504 translates along the length of the shaft 502 during roll operations, the length and pitch of the lead screw 509 may limit the number of elongated shaft roll revolutions allowed by the device 501. Consequently, longer devices with longer lead screws will generally allow greater shaft roll revolutions than shorter devices with shorter lead screws. Accordingly there may be a longer instrument base 503 to accommodate more rotations from a given lead screw with a specific pitch. Moreover, since wraps around the shaft 502 are directly proportional to the revolutions the shaft 502 may roll, an excessive number of wraps may heavily influence friction. Alternatively, a tighter pitch or steeper angle in the grade of the lead screw 509 may also affect roll revolutions and thus the length of the instrument base.

Figure 6A:
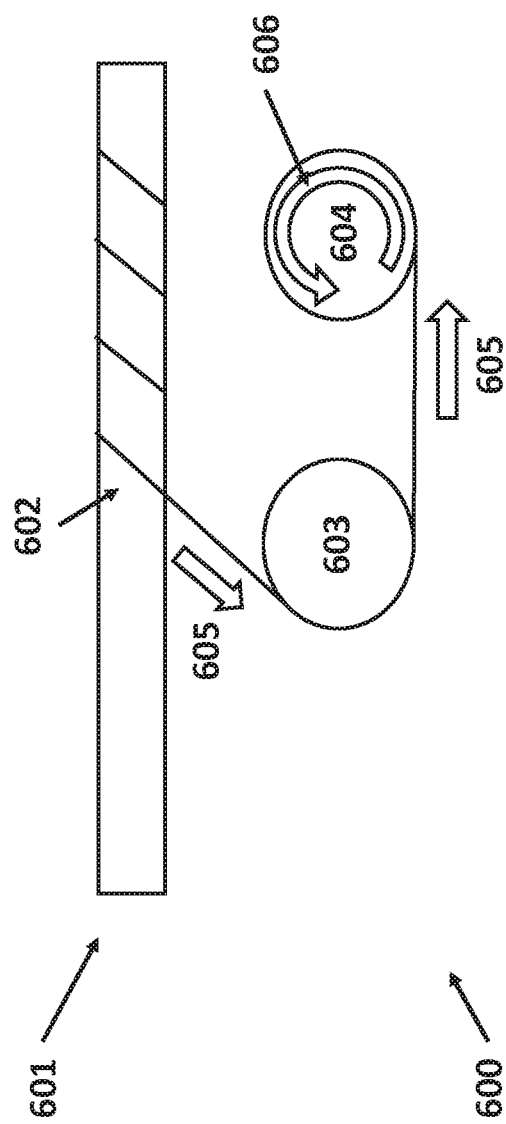
FIG. 6A illustrates how a single pull wire may be tensioned in order to generate articulation in the elongated shaft.
Figure 6B:
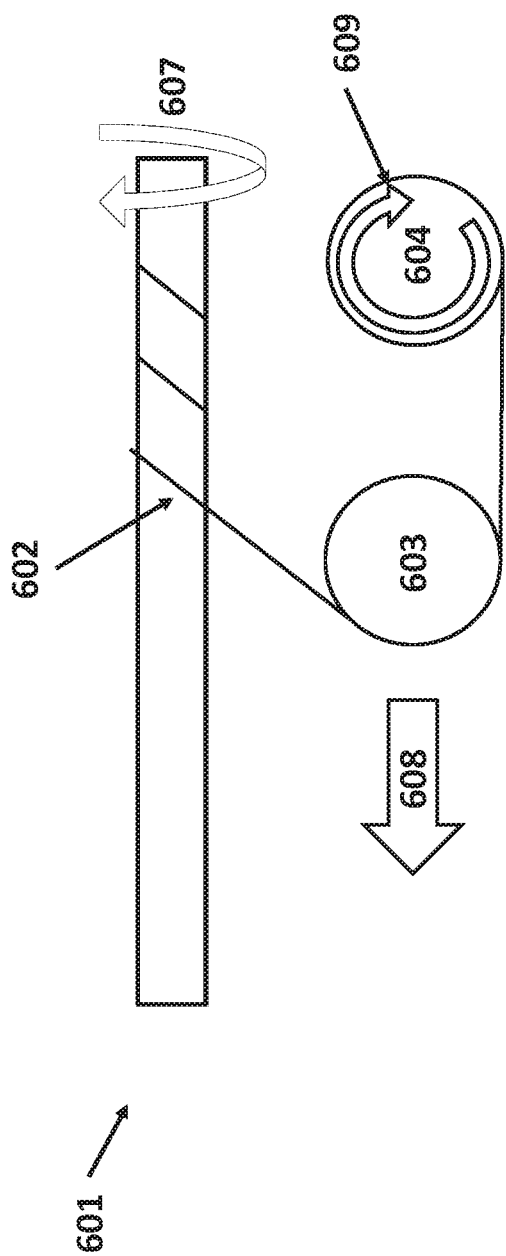
FIG. 6B illustrates how the elongated shaft, pull wire, angled idler, and spool components from FIG. 6A maintain a consistent helical pitch when rolling the elongated shaft clockwise.
Figure 6C:
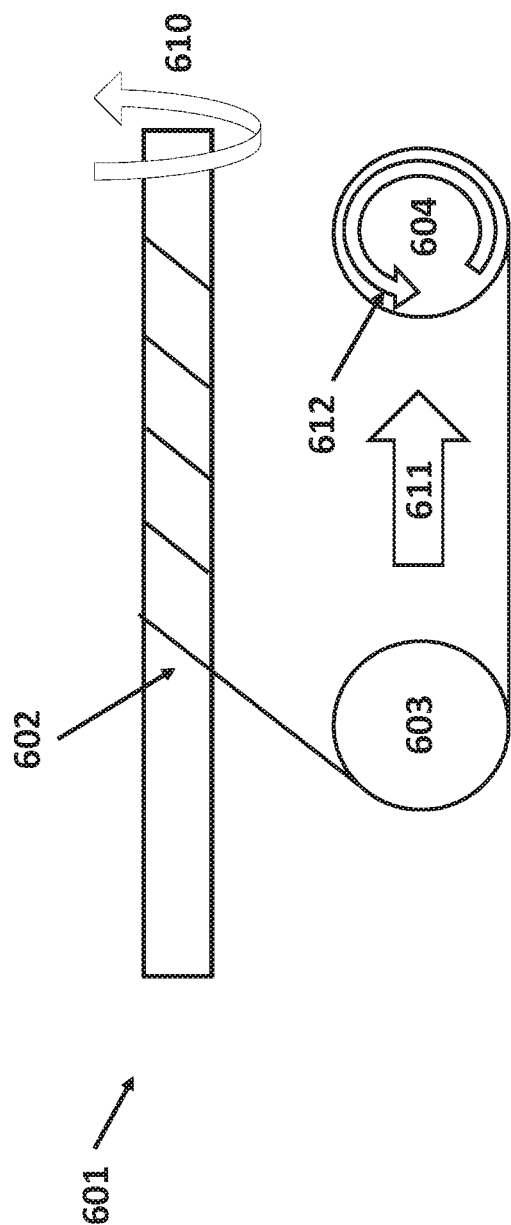
FIG. 6C illustrates how the elongated shaft, pull wire, angled idler, and spool from FIGS. 6A, 6B maintain a consistent helical pitch when rolling the elongated shaft counter-clockwise.

FIGS. 6A-6C illustrates roll and articulation operations of endoscopic device 501 with respect to a single pull wire, single angled idler, and single spool. Specifically, FIG. 6A illustrates how a single pull wire may be tensioned in order to generate articulation in the elongated shaft. As shown in isolated top view 600, exemplar elongated shaft 601 may already be wrapped with a single pull wire 602. Similar to the earlier embodiments, pull wire 602 may be directed to spiral onto a portion of the elongated shaft 601 by angled idler 603. The pull wire 602 may also be controlled via spool 604, whose rotational motion may generate compressive force along the length of the pull wire 602. Thus, in order to tension pull wire 602 and articulate the distal tip of shaft 601, shaft 601 and idler 603 remain static while spool 604 rotates in the direction indicated by arrow 606 to create compression tension along pull wire 602 in the direction indicated by arrow 605. That "pulling" force is then transferred along the length of pull wire around idler 603, along shaft 601 until reaching the distal tip, where the pull wire 602 is fixedly coupled. As the pull wire 602 is fixedly coupled to the end of the distal end of the elongated shaft 601, compressive tension results in bending or articulating of the elongated shaft 601.

FIG. 6B illustrates how the elongated shaft, pull wire, angled idler, and spool components from FIG. 6A maintain a consistent helical pitch when rolling the elongated shaft clockwise. In order to roll the elongated shaft 601, the angled idler 603 may be moved simultaneously to maintain a consistent takeoff angle in the pull wire 602. When rolling the elongated shaft 601 in the clockwise direction indicated by arrow 607, in order to maintain the helical pitch, the angled idler 603 may be translated longitudinally relative to the shaft 601 in the direction indicated by arrow 608. Translating the idler 603 while shaft 601 rotates ensures that the pull wire 602 is wrapped around shaft 601 with a consistent helix by ensuring that the pull wire 602 always has the same takeoff angle from angled idler 603. Put differently, translating the idler 603 in the direction of arrow 608 ensures that the pull wire 602 is "wrapped" around unwrapped portions of the shaft 601 at an even pitch, rather than wrapping in an uneven pitch or even on already-wrapped portions of the shaft 601. Due to the translation of the idler tension in the pull wire 602 requires that the spool 604 be rotated in direction indicated by arrow 609 in order to allow additional length of the pull wire 602 to be wrapped around shaft 601 at a consistent takeoff angle. In effect, the spool 604 must unwrap additional length of the pull wire 602 from itself in order to accommodate the additional wrapping of the pull wire 602 around the shaft 601 and the translation of the idler 603. The rate at which idler 603 advances in direction 608 relative to the rotation of 601 in direction 607 ensures that pull wire 602 is always encounters shaft 601 at the same takeoff angle, which maintains a consistent helical pitch and angle around the shaft 601.

FIG. 6C illustrates how the elongated shaft, pull wire, angled idler, and spool from FIGS. 6A, 6B maintain a consistent helical pitch when rolling the elongated shaft counter-clockwise. When rolling the elongated shaft 601 in the counter-clockwise direction indicated by arrow 610, in order to maintain the helical pitch, the angled idler 603 may be translated longitudinally relative to the shaft 601 in the direction indicated by arrow 611. Translating the idler 603 while shaft 601 rotates ensures that the pull wire 602 has the same takeoff angle as it unwraps from shaft 601. Put differently, translating the idler 603 in the direction of arrow 611 ensures that the pull wire 602 is "unwrapped" with the same takeoff angle from the shaft 601 preserving the helical pitch and angle of the pull wire 602 still wrapped about the shaft 601. Due to the translation of the idler 603, the formation of slack in the pull wire 602 requires that the spool 604 be rotated in direction indicated by arrow 612 in order to collect the loose length of pull wire 602. In effect, the spool 604 must wrap and collect additional length of the pull wire 602 to accommodate the "unwrapping" of the pull wire 602 from the shaft 601 and the translation of the idler 603. The angle of the idler 603 ensures that pull wire 602 is always unwrapped from the shaft 601 at the same point, helping ensure a consistent helical pitch and angle about shaft 601.

The embodiments in FIGS. 5A-5D, 6A-6C enable three-degrees of freedom at the tip of a flexible, articulating device while maintaining a static instrument base (503). By constraining the pull wire helical pitch on the elongated shaft during roll operations, tension variability is minimized and articulation controls are simplified. Furthermore, the design allows for functional adjustments and fine-tuning of features, such as shaft revolutions and relative carriage speed, merely by altering the features of the lead screw and transmission gears. Different configurations of helical wire pitches and the number of revolutions can be attained simply by varying the length of the lead screw, pitch of the threads, and its associated drivetrain to the main shaft. Moreover, the compact design also allows for electronics (such as circuit board 527 in FIG. 5A) and other internal features to be placed within the instrument base.

The embodiments in FIGS. 5A-5D, 6A-6C allow the ability to rotate or "roll" the flexible shaft after a long journey through a tortuous path in the patient's anatomy. For example, after traversing through a long and tortuous path, endoscopic device 501 may articulate elongated shaft 502 and roll elongated shaft 502 in order to reach to an operative site. In some circumstances, it may be useful to first roll elongated shaft 502 and then articulate elongated shaft 502 in order to reach certain locations with the patient's anatomy. Use of roll may also provide improved access to operative sites where robotically-driven articulation may be insufficient and ineffective, a circumstance that may occur as a result of traversing through tortuous paths.

In addition to improved reach, the disclosed embodiments may also enable roll to reduce braking static friction when traversing through a tortuous path. For example, rolling elongated shaft 502 while simultaneously extending into an anatomical lumen may reduce friction caused from contact with the lumen walls. Furthermore, rolling the elongated shaft 502 may also reduce friction caused by contact at anatomical transitions.

In practice, rolling and subsequently articulating endoscopic device 501 within an anatomical lumen involves several mechanical steps. For example, the instrument interface would first rotate lead screw output shaft 526 in order to rotate right angle gear transmission 525. In response to rotating right angle gear transmission 525, lead screw 509 would rotate. The rotation of the lead screw 509 would result in the motion of several components within the instrument base 503. Firstly, the rotation of the lead screw 509 would transmit angular motion to shaft transmission gear 523 which would cause shaft 502 to rotate.

Secondly, rotation of the lead screw 509 would also cause idler carriage 504 to laterally move along the shaft 502. Depending on the direction of rotation and the thread of lead screw 509, the idler carriage 504 may either move forward towards the distal tip of the elongated shaft 502 or back towards the proximal end of the elongated shaft 502.

The roll of elongated shaft 502 creates tension on pull wires 518, 519, 520, 521. To compensate and alleviate the tension, instrument interface would rotate output shafts 516 and 517 (and their associated concentrically-aligned sub-shafts) in order to reduce tension in the pull wires as explained in FIGS. 6B and 6C. Once the roll is complete, the tension-compensation process may terminate. After rotating the shaft 502, the distal tip of the shaft 502 may then be articulated in order to reach the desired operative site. Tensioning the appropriate pull wire in order to articulate may be executed using the technique described in FIG. 6A.

The aforementioned embodiments of the present invention may be designed to interface with robotics platform such as those disclosed in the aforementioned patent applications that are incorporated by reference. For example, the embodiments in FIGS. 5A-5D, 6A-6D may be configured to be driven by an instrument drive mechanism or an instrument device manipulator that is attached to the distal end of a robotic arm through a sterile interface, such as a drape. As part of a larger robotics system, robotic control signals may be communicated from a remotely-located user interface, down the robotic arm, and to the instrument device manipulator to control the instrument or tool.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A medical instrument configured for use with a robotic system, the medical instrument comprising:
   an instrument base configured to couple to a robotic drive mechanism of the robotic system;
   an elongate shaft coupled to the instrument base, the elongate shaft having a distal end;
   a pull wire fixedly coupled to the distal end of the elongate shaft, the pull wire being configured to actuate the elongate shaft; and
   a rotatable spool in the instrument base, the rotatable spool being configured to direct the pull wire to the elongate shaft at an angle,
   wherein the rotatable spool is configured to translate in coordination with actuation of the elongate shaft to control the angle of the pull wire relative to the elongate shaft.

2. The medical instrument of claim 1, wherein translation of the rotatable spool is configured to maintain the angle at a consistent angle relative to the elongate shaft.

3. The medical instrument of claim 1, wherein the rotatable spool is configured to translate longitudinally relative to the elongate shaft.

4. The medical instrument of claim 1, further comprising:
   a screw in the instrument base that runs parallel to the elongate shaft, the screw being coupled to the rotatable spool to urge translation of the rotatable spool in coordination with the actuation of the elongate shaft.

5. The medical instrument of claim 4, further comprising:
   a carriage configured to hold the rotatable spool, wherein the carriage is configured to translate along the screw in coordination with the actuation of the elongate shaft.

6. The medical instrument of claim 1, wherein the rotatable spool is configured to translate towards the distal end of the elongate shaft or towards a proximal end of the elongate shaft in coordination with the actuation of the elongate shaft.

7. The medical instrument of claim 1, wherein the instrument base comprises a robotic interface configured to couple to the robotic drive mechanism, wherein angular motion in the robotic interface is configured to exert a pulling force on the pull wire.

8. A medical robotic system comprising:
   a medical instrument comprising an elongate shaft, a rotatable spool, and a pull wire arranged around the rotatable spool and fixedly coupled to the elongate shaft, wherein the pull wire exits the rotatable spool at an angle; and
   a robotic drive mechanism coupled to the medical instrument, the robotic drive mechanism being configured to actuate the elongate shaft by applying tension to the pull wire, wherein the robotic drive mechanism is further configured to control the angle of the pull wire by translating the rotatable spool in coordination with applying the tension to the pull wire.

9. The medical robotic system of claim 8, further comprising a robotic arm having a distal end attached to the robotic drive mechanism.

10. The medical robotic system of claim 8, wherein the pull wire is fixedly coupled to a distal end of the medical instrument.

11. The medical robotic system of claim 8, wherein the translating of the rotatable spool is configured to maintain the angle at a consistent angle as the rotatable spool translates.

12. The medical robotic system of claim 8, further comprising:
   a screw coupled to the rotatable spool, the screw being configured to urge the translating of the rotatable spool.

13. The medical robotic system of claim 8, wherein the robotic drive mechanism is configured to translate the rotatable spool towards a proximal end or a distal end of the elongate shaft.

14. The medical robotic system of claim 8, wherein the robotic drive mechanism is configured to drive angular motion in a robotic interface of the medical instrument, the angular motion creating rotational motion in the spool.

15. The medical robotic system of claim 8, wherein the robotic drive mechanism is configured to translate the rotatable spool longitudinally relative to the elongate shaft.

16. A medical instrument configured for use with a robotic system, the medical instrument comprising:
   an elongate shaft configured to be inserted into an anatomy of a patient;
   a pull wire coupled to the elongate member;
   a robotic interface coupled to the pull wire, the robotic interface being configured to exert a pulling force on the pull wire to control a degree of freedom of the elongate member; and
   a redirect member configured to translate simultaneously with exertion of the pulling force on the pull wire,
   wherein the pull wire is routed around the redirect member so that is exits the redirect member at an angle, and
   wherein translation of the redirect member maintains the angle at which the pull wire exits the redirect member.

17. The medical instrument of claim 16, wherein the redirect member comprises a rotatable spool, a rotatable pulley, or a surface.

18. The medical instrument of claim 16, wherein the pull wire is fixedly coupled to a distal tip of the elongate shaft so that the pulling force is transferred to the distal tip of the elongate shaft upon exertion of the pulling force by the robotic interface.

19. The medical instrument of claim 16, wherein the redirect member is configured to translate longitudinally relative to the elongate shaft.

20. The medical instrument of claim 16, further comprising:
   a screw coupled to the redirect member, the screw being configured to urge the translating of the redirect member.

* * * * *